United States Patent [19]

Eckstein et al.

[11] 4,298,010

[45] Nov. 3, 1981

[54] BREATHING ALCOHOL TESTING DEVICE

[75] Inventors: Wolfgang Eckstein, Sereetz; Horst Rabenecker, Klein Parin, both of Fed. Rep. of Germany

[73] Assignee: Drägerwerk Aktiengesellschaft, Fed. Rep. of Germany

[21] Appl. No.: 89,463

[22] Filed: Oct. 30, 1979

[30] Foreign Application Priority Data

Nov. 8, 1978 [DE] Fed. Rep. of Germany ....... 2848337

[51] Int. Cl.³ .............................................. A61B 5/00
[52] U.S. Cl. ................................................... 128/719
[58] Field of Search ............... 128/716, 718, 719, 724, 128/730

[56] References Cited

U.S. PATENT DOCUMENTS

| 3,734,692 | 5/1973 | Lucker et al. | 128/730 |
| 3,824,168 | 7/1974 | Oswin et al. | 128/719 |
| 3,962,917 | 6/1976 | Terapa | 128/724 |
| 4,220,162 | 9/1980 | Clark et al. | 128/724 |

Primary Examiner—William E. Kamm
Attorney, Agent, or Firm—McGlew and Tuttle

[57] ABSTRACT

A breathing alcohol testing device comprises a tube for blowing expiration air therethrough which has a first air entrance end and an opposite second end with means for accommodating a testing tube containing a gas detection substance. A pump is connected to the tube for moving expiration air through the tube and pressure sensing means are associated with the tube for sensing the pressure adjacent the entrance end for regulating the pump in accordance with the sensed pressure. In addition to the sensing of pressure, velocity may also be sensed and a control device is connected between the sensors and the pump so as to regulate the pump to start after the tube is engaged in a person's mouth and he begins expiring his breath into the tube and a certain pressure is generated at a certain velocity. The pump may be provided directly in the line ahead of the gas testing device for forcing the breathing air through the tube and through the testing device or it may be provided downstream of the testing device. When the pump is located downstream of the testing device the tube is provided with an additional socket having a valve regulation for admitting air into the tube in accordance with the sensed pressure conditions and velocity conditions in the operation of the pump.

9 Claims, 2 Drawing Figures

BREATHING ALCOHOL TESTING DEVICE

FIELD AND BACKGROUND OF THE INVENTION

This invention relates in general to devices for testing the contents of a person's breath to determine the presence of alcohol, and in particular to a new and useful device and method for effecting the testing of the expiration air for alcohol.

Breathing alcohol testing devices must be carried along by the user and must be ready for use. The measuring result should be sufficiently accurate, despite the frequently adverse circumstances under which the measurements must be made in the open air. The lack of cooperation of the test person must not affect the measuring unit.

In a known breathing alcohol testing device, the test person blows directly into a testing tube through a mouthpiece. The amount of expiration gas which is necessary to determine the alcohol concentration in the expiration air, is found by means of a measuring bag arranged behind the testing tube, which must be inflated. This known method requires tubes with a low resistance in order to keep the blowing effort of the test person within limits. The breathing alcohol testing tubes must therefore have a relatively large cross section and may only have a short preparation layer. Since the length of the discoloration of the preparation is a measure of the alcohol content in the expiration air, an extension would mean a greater measuring sensitivity (German Pat. No. 10 52 630).

A known device for measuring the expiration gas mixture by means of a breathing alcohol testing tube has a breath sample chamber with a defined maximum volume. It is brought by the breath from a starting position into an end position, so that it contains a breath sample of a defined volume. When the breath sample chamber is full, a pump goes into action with which the breathing air contained in the breath sample chamber is fed over a line to and through the breathing alcohol testing tube. The guidance of the breathing air over the breath sample chamber leads to difficulties, caused by cooling. In order to avoid this, the entire device, not only the chamber, but all lines are heated. The device is therefore complicated, voluminous, and requires principally a heating period before use (German Pat. No. 12 98 311).

SUMMARY OF THE INVENTION

The object of the invention is to provide a breathing alcohol testing device, using a breathing alcohol testing tube which requires no blowing effort on the part of the test person and still supplies measuring results of sufficient accuracy.

In accordance with the invention, a breathing alcohol testing device comprises a tube for blowing expiration air therethrough which has a first air entrance end an opposite second end with holder means for holding a gas testing substance. The gas testing substance is advantageously contained in a testing tube through which the air is passed to turn the substance a selected color or brightness in accordance with the presence of alcohol. A pump is connected to the tube for moving the expiration air through the tube and it operates after the tube is engaged by the mouth of a person and he begins expiring into the tube to build up the pressure therein. The construction is such that the pump forces the expiration air through the tube after expiration has begun and a light is provided for indicating that this is going on so that it may be carried out for a predetermined time interval.

In accordance with a method of the invention a person's breath is tested for the presence of alcohol using a breathing alcohol testing device which includes a pump connected thereto and a tube for directing air therethrough and through a testing tube containing an alcohol sensitive substance which comprises engaging the tube with the person's mouth and the commencing of expiration, and thereafter causing the pump to work to force the air through the tube and through the testing substance.

Since the pump can only be started when a minimum pressure has been attained by the test person behind the mouthpiece, this ensures that actually expiration air is fed through the device. In order to make it easier for the test person, even when using testing tubes with a higher resistance, hence greater sensitivity, a pump takes over the feeding of the expiration through the testing tube, either as a pressure or as a suction pump.

The total amount of breathing gas necessary for the measurement is determined with a velocity sensor and the data fed into a control unit, the pump is then shut off. One embodiment of the invention permits scavenging the shuttle air in a simple manner, so that only part of the expiration air is fed through the testing tube that contains the actual portion of alcohol.

The breathing alcohol device according to the invention requires no chamber or bag, etc. to secure the measuring volume. It can therefore be small, which is suitable for a portable device that is preferably carried on the person. Sensitive valves with their connection lines and control means are not necessary. Due to the possibility of using breathing alcohol testing tubes with a higher resistance, the measuring sensitivity and thus the measuring accuracy are substantially increased.

In accordance with the invention, an improved breathing alcohol testing device for determining the alcohol content in the expiratory air of a person is provided. The device is of the type having an elongated detector tube with a bore extending therethrough from an entrance opening to an outlet opening, a gas detecting substance mounted within the bore throughout a length thereof intermediate the entrance opening and the outlet opening for the passage therethrough of the air to be tested. The gas testing substance is of the type which discolors responsive to the alcohol content in the air and length of the discoloration of the substance is a measure of the alcohol content. The improvement comprises a pump connected to the tube for removing the expiratory air to be tested through the tube. A pressure sensor associated with the tube for sensing the pressure therein is mounted adjacent the entrance opening upstream of the gas testing substance. Control means connected to the pressure sensor and to the pump is provided for starting the pump at a predetermined pressure so that the pump forces the expiratory air through the detector tube and through the gas testing substance. In accordance with a preferred embodiment of the invention, a velocity sensor is located in the detector tube adjacent the pressure sensor and is connected to the control means. The control means is operative to measure the velocity of the expiratory gas and to shut off the pump when a given amount of the expiratory gas has passed through the detector tube.

In accordance with still another preferred embodiment of the invention, a connection tube is mounted to the detector tube and the entrance opening. The connection tube has a blow opening for receiving expiratory air to be tested and an exit opening for the passage of the expiratory air therethrough. The connection tube includes a socket tube connected to the connection tube intermediate the blow opening and the exit opening for selective discharge of expiratory air upstream of the detector tube. The pump is connected to the detector tube downstream of the gas testing substance.

Accordingly, it is an object of the invention to provide a breathing alcohol testing device which comprises a tube for blowing expiration air therethrough which has a first air entrance and a second opposite end with holder means for holding a gas testing substance and with a pump connected to the tube for moving the expiration air therethrough and connected to pressure sensing means associated with the tube adjacent the entrance end which in turn is connected to control means and the pump so that the pump is regulated after a predetermined pressure is reached in the tube to pump the expiration air therethrough.

A further object of the invention is to provide a method of testing for alochol which comprises causing a person to blow through a testing tube which contains an alcohol sensitive substance and after initial blowing causing the expiration air to be pumped through the tube and through the substance.

A further object of the invention is to provide a testing device which is simple in design, rugged in construction and economical to manufacture.

The various features of novelty which characterize the invention are pointed out with particulality in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 2:
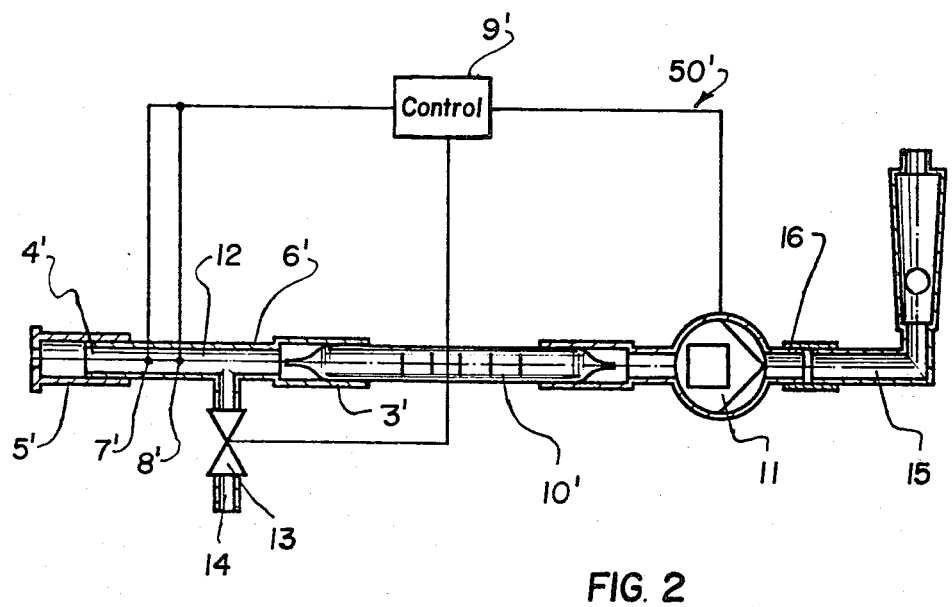
FIG. 2 is a view similar to FIG. 1 but showing another embodiment of the device.

Referring to the drawings, in particular the invention embodied therein comprises a breathing alcohol testing device generally designated 50 which includes a tube 1 for blowing expiration air therethrough having a first air entrance end 1a with an opening 4 therethrough for receiving expiration air which is passed through the tube and through a pump 2 therein to an opposite or second end 3 having means for holding a gas testing device such as a testing tube 10. In accordance with the invention, the pump 2 may be arranged either upstream of the gas testing device 10 or downstream of the gas testing device 10' as shown in FIG. 2.

Figure 1:
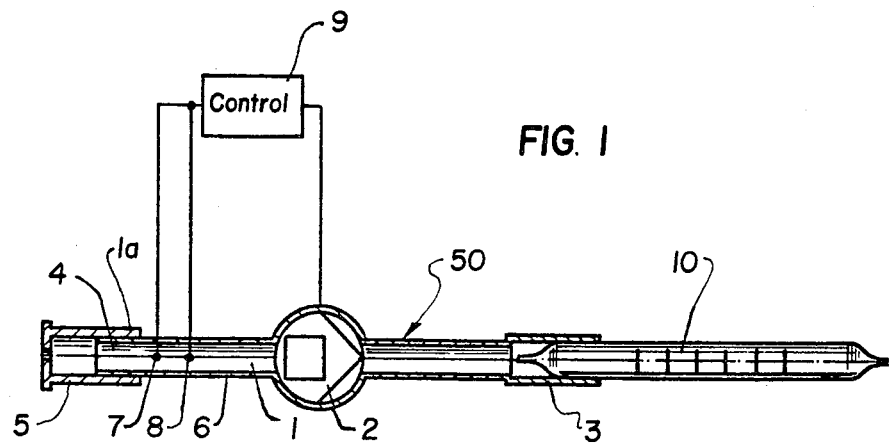
FIG. 1 is a sectional view of a testing device constructed in accordance with the invention.

The breathing alcohol testing device according to FIG. 1 consists of a first connection piece 1 or expiration air passage tube 1 with a pressure pump 2 therein and having one end forming testing tube receiver 3. A replaceable mouthpiece 5 is pushed over a blow opening 4 at the opposite end of the tube 1. A portion 6 of the tube between pressure pump 2 and blow opening 4 contains directly behind blow opening 4 a pressure sensor 7 and a velocity sensor 8. Both sensors, 7 and 8 supply their values to a control unit 9, which in turn controls pressure pump 2.

Breathing alcohol testing tube 10 is held gas-tight in testing tube receiver 3. Pressure sensor 7 lights up a signal lamp in control unit 9 as long as a minimum pressure is maintained or exceeded by the test person in the first connection piece 1 when blowing-in expiration air.

When the minimum pressure is attained, pressure pump 2 goes into action and feeds the expiration gas through breathing alcohol testing tube 10. Velociy sensor 8 measures the velocity of flow of the expiration air passing through the first connection piece 1, and thus also through breathing alcohol testing tube 10. Control unit 9 computes from this velocity the time that is required to feed the amount of expiration air necessary for the test through the testing tube. At the end of this period pressure pump 2 is shut off.

In the breathing alcohol testing device 50' according to FIG. 2, a pump 11 in the form of a suction pump 11 is arranged in a tubing 16 behind breathing alcohol testing tube 10. A second connection piece or tube 12 has in front of a testing tube receiver portion 3' a socket 14 with a valve 13 to be opened and closed by a control unit 9'. The shuttle air can be blown out from the alveolars, the pharyngeal cavity and the mouth over socket 14 before suction pump 11 starts, or if a socket 14 is also provided in the first connection piece 1, before pressure pump 2 starts. This ensures that the expiration air entering breathing alcohol testing tube 10 contains the actual amount of breathing alcohol.

In order to check the flow of expiration air, flow meter 15 can be connected to the blow opening of breathing alcohol testing tube 10 or of tubing 16.

While specific embodiments of the invention have been shown and described in detail to illustrate the application of the principles of the invention, it will be understood that the invention may be embodied otherwise without departing from such principles.

What is claimed is:

1. An improved breathing alcohol testing device for determining the alcohol content in the expiratory air of a person, the device being of the type having an elongated detector tube with a bore extending therethrough from an entrance opening to an outlet opening, a gas testing substance mounted within the bore, throughout a length thereof, intermediate the entrance opening and the outlet opening for passage therethrough of the air to be tested, the gas testing substance being of the type which discolors responsive to the alcohol content in the air and wherein the length of the discoloration of the substance is a measure of the alcohol content, wherein the improvement comprises a pump connected to the detector tube for moving the expiratory air to be tested through the detector tube, pressure sensing means associated with the tube for sensing the pressure therein adjacent said entrance opening upstream of the gas testing substance, and control means connected to said pressure sensing means and to said pump for starting said pump at a predetermined pressure so that said pump forces the expiratory air through the detector tube and through the gas testing substance.

2. An improved breathing alcohol testing device according to claim 1, further comprising a velocity sensor located in the detector tube adjacent said pressure sensing means and connected to said control means, said control means measuring the velocity of the expiratory gas, and said control means being operable to shut off said pump when a given amount of the expiratory gas has passed through the detector tube.

3. An improved breathing alcohol testing device according to claim 2, further comprising a connection tube mounted to the detector tube at the entrance opening, said connection tube having a blow opening for receiving expiratory air and an exit opening for the passage of the expiratory air therethrough, said connection tube including a socket tube connected to said connection tube intermediate said blow opening and said exit opening for the selective discharge of expiratory air upstream of the detector tube, and wherein said pump is connected to the detector tube downstream of the gas testing substance.

4. An improved breathing alcohol testing device according to claim 3, further comprising a valve in said socket tube operatively connected to said control means, said valve operable responsive to said control means to open said socket tube.

5. An improved alcohol testing device according to claim 4, further comprising a flow meter connected to the detector tube downstream of the gas testing substance for measuring the flow therethrough.

6. An improved alcohol testing device according to claim 1, wherein said pump is located in the detector tube between the entrance and outlet openings.

7. An improved breathing alcohol testing device according to claim 1, further comprising a connection tube mounted to the detector tube at the entrance opening, said connection tube having a blow opening for receiving expiratory air and an exit opening for the passage of the expiratory air therethrough, said connection tube including a socket tube connected to said connection tube intermediate said blow opening and said exit opening for the selective discharge of expiratory air upstream of the detector tube, and wherein said pump is connected to the detector tube downstream of the gas testing substance.

8. An improved breathing alcohol testing device according to claim 7, further comprising a valve in said socket tube operatively connected to said control means, said valve being operable responsive to said control means to open said socket tube.

9. An improved breathing alcohol testing device according to claim 1, further comprising a flow meter connected to the detector tube downstream of the gas testing substance for measuring the flow therethrough.

* * * * *